(12) United States Patent
Nakauchi et al.

(10) Patent No.: US 10,383,836 B2
(45) Date of Patent: Aug. 20, 2019

(54) COMPOSITION FOR DECREASING HEMATOPOIETIC STEM CELLS, AND METHOD FOR PRODUCING SAME

(71) Applicant: THE UNIVERSITY OF TOKYO, Bunkyo-ku (JP)

(72) Inventors: Hiromitsu Nakauchi, Tokyo (JP); Satoshi Yamazaki, Tokyo (JP); Yuki Taya, Tokyo (JP)

(73) Assignee: THE UNIVERSITY OF TOKYO, Bunkyo-ku (JP)

( * ) Notice: Subject to any disclaimer, the term of this patent is extended or adjusted under 35 U.S.C. 154(b) by 0 days.

(21) Appl. No.: 15/528,182

(22) PCT Filed: Nov. 25, 2015

(86) PCT No.: PCT/JP2015/083088
§ 371 (c)(1),
(2) Date: Sep. 1, 2017

(87) PCT Pub. No.: WO2016/084850
PCT Pub. Date: Jun. 2, 2016

(65) Prior Publication Data
US 2017/0354626 A1    Dec. 14, 2017

(30) Foreign Application Priority Data
Nov. 25, 2014 (JP) ................. 2014-237874

(51) Int. Cl.
| | |
|---|---|
| *A61K 31/198* | (2006.01) |
| *A61K 45/06* | (2006.01) |
| *A61K 31/70* | (2006.01) |
| *A61K 33/00* | (2006.01) |
| *C12Q 1/04* | (2006.01) |

(Continued)

(52) U.S. Cl.
CPC ............ *A61K 31/198* (2013.01); *A23L 33/30* (2016.08); *A23L 33/40* (2016.08); *A61K 31/70* (2013.01); *A61K 33/00* (2013.01); *A61K 35/28* (2013.01); *A61K 45/06* (2013.01); *A61P 3/02* (2018.01); *A61P 43/00* (2018.01); *C12Q 1/04* (2013.01); *G01N 33/5094* (2013.01); *A23V 2002/00* (2013.01); *A61K 2035/124* (2013.01)

(58) Field of Classification Search
None
See application file for complete search history.

(56) References Cited

U.S. PATENT DOCUMENTS

2013/0252335 A1    9/2013   Kume et al.

FOREIGN PATENT DOCUMENTS

| JP | 59-53429 A | 3/1984 |
|---|---|---|
| JP | 62-135420 A | 6/1987 |
| WO | WO 2012/056997 A1 | 5/2012 |

OTHER PUBLICATIONS

Sugiyama et al., Immunity, 25:977-988 (2006).*

(Continued)

*Primary Examiner* — Thomas J. Visone
(74) *Attorney, Agent, or Firm* — Oblon, McClelland, Maier & Neustadt, L.L.P.

(57) ABSTRACT

Problem to be Solved
The present invention provides a technique replacing radiation exposure in decreasing or eliminating hematopoietic stem cells in an animal (particularly human) body.
Solution
A parenteral nutrition formula or an enteral nutrition formula substantially free of valine.

12 Claims, 15 Drawing Sheets

(51) Int. Cl.
*A23L 33/00* (2016.01)
*A61K 35/28* (2015.01)
*G01N 33/50* (2006.01)
*A61P 3/02* (2006.01)
*A61P 43/00* (2006.01)
*A61K 35/12* (2015.01)

(56) References Cited

OTHER PUBLICATIONS

Tabbara et al., Arch. Intern. Med.,162:1558-1566 (2002).*
Yoshida et al., Arg. Biol. Chem., 33(1):43-49 (1969).*
International Search Report dated Sep. 12, 2017 in PCT/JP2017/028333 (with English translation of categories of cited documents).
Narihide Goseki, et al., "Treatment of Adenocarcinoma by Combination of Intravenous Nutrition using Special Amino Acid Preparation and Anticancer Drugs (RT-Therapy)", Journal of Japanese Society of Gastroenterology, vol. 77, No. 1, 1980, p. 112 (with English language translation).
International Search Report dated Feb. 2, 2016 in PCT/JP2015/083088 (with English Translation).
Arthur Kornberg et al., "Granulocytopenia and Anemia in Rats Fed Diets of Low Casein Content", Science. vol. 103, No. 2682, May 24, 1046, pp. 646-648 and cover page.
Masahiro Chin et al., "Special Edition, Nutrition—Immunity Correlation, Amino Acid Imbalance and Immunocompetence", Biotherapy, vol. 11, No. 4, Apr. 1997, pp. 518-523 (with English Translation).
Masahiro Chin et al., "Establishment of TPN Administration System and Application for Valine Deficient Amino Acid Imbalance Experiment in Mice.", The Japanese Journal of Surgical Metabolism and Nutrition, vol. 31, No. 3, Jun. 1997, p. 147 and cover page, (with English Translation).
Yusuke Nakauchi et al., "Special Edition, Hematopoietic Stem Cell Transplantation and Clinical Examination", Medical Technology, vol. 40, No. 8, Aug. 2012, pp. 854 to 859, (with English Translation).
Hirokazu Okumura, "Basic and Current Status of Allogeneic Hematopoietic Stem Cell Transplantation", Medical Journal of Toyama Prefectural Central Hospital, vol. 36. No. 1-2, Mar. 2013, pp. 1-7 and cover page, (with English Translation).

* cited by examiner

| AMINO ACID CONTENT (mg/L) | CONVENTIONAL DIET | AMINO ACID COMPOSITION IN MEDIUM | | | | | | | | | | |
|---|---|---|---|---|---|---|---|---|---|---|---|---|
| | | A(-Ala) | C(-Cys) | D(-Asp) | E(-Glu) | F(-Phe) | G(-Gly) | H(-His) | I(-Ile) | K(-Lys) | L(-Leu) | M(-Met) |
| ALANINE | 2.225 | 0 | 2.225 | 2.225 | 2.225 | 2.225 | 2.225 | 2.225 | 2.225 | 2.225 | 2.225 | 2.225 |
| ARGININE HCl | 73.75 | 73.75 | 73.75 | 73.75 | 73.75 | 73.75 | 73.75 | 73.75 | 73.75 | 73.75 | 73.75 | 73.75 |
| ARGININE | 100 | 100 | 100 | 100 | 100 | 100 | 100 | 100 | 100 | 100 | 100 | 100 |
| ANHYDROUS ASPARAGINE | 25 | 25 | 25 | 25 | 25 | 25 | 25 | 25 | 25 | 25 | 25 | 25 |
| ASPARAGINE H₂O | 3.75 | 3.75 | 3.75 | 3.75 | 3.75 | 3.75 | 3.75 | 3.75 | 3.75 | 3.75 | 3.75 | 3.75 |
| ASPARTIC ACID | 13.325 | 13.325 | 13.325 | 0 | 13.325 | 13.325 | 13.325 | 13.325 | 13.325 | 13.325 | 13.325 | 13.325 |
| CYSTEINE 2HCl | 48.245 | 48.245 | 0 | 48.245 | 48.245 | 48.245 | 48.245 | 48.245 | 48.245 | 48.245 | 48.245 | 48.245 |
| CYSTEINE HCl·H₂O | 8.78 | 8.78 | 0 | 8.78 | 8.78 | 8.78 | 8.78 | 8.78 | 8.78 | 8.78 | 8.78 | 8.78 |
| GLUTAMIC ACID | 13.675 | 13.675 | 13.675 | 13.675 | 0 | 13.675 | 13.675 | 13.675 | 13.675 | 13.675 | 13.675 | 13.675 |
| GLUTAMINE | 332.5 | 332.5 | 332.5 | 332.5 | 332.5 | 332.5 | 332.5 | 332.5 | 332.5 | 332.5 | 332.5 | 332.5 |
| GLYCINE | 14.375 | 14.375 | 14.375 | 14.375 | 14.375 | 14.375 | 0 | 14.375 | 14.375 | 14.375 | 14.375 | 14.375 |
| HISTIDINE HCl·H2O | 15.74 | 15.74 | 15.74 | 15.74 | 15.74 | 15.74 | 15.74 | 0 | 15.74 | 15.74 | 15.74 | 15.74 |
| HISTIDINE | 7.5 | 7.5 | 7.5 | 7.5 | 7.5 | 7.5 | 7.5 | 0 | 7.5 | 7.5 | 7.5 | 7.5 |
| HYDROXYPROLINE | 10 | 10 | 10 | 10 | 10 | 10 | 10 | 10 | 10 | 10 | 10 | 10 |
| ISOLEUCINE | 297.35 | 297.35 | 297.35 | 297.35 | 297.35 | 297.35 | 297.35 | 297.35 | 0 | 297.35 | 297.35 | 297.35 |
| LEUCINE | 54.525 | 54.525 | 54.525 | 54.525 | 54.525 | 54.525 | 54.525 | 54.525 | 54.525 | 54.525 | 0 | 54.525 |
| LYSINE HCl | 65.625 | 65.625 | 65.625 | 65.625 | 65.625 | 65.625 | 65.625 | 65.625 | 65.625 | 0 | 65.625 | 65.625 |
| METHIONINE | 16.12 | 16.12 | 16.12 | 16.12 | 16.12 | 16.12 | 16.12 | 16.12 | 16.12 | 16.12 | 16.12 | 0 |
| PHENYLALANINE | 25.24 | 25.24 | 25.24 | 25.24 | 25.24 | 0 | 25.24 | 25.24 | 25.24 | 25.24 | 25.24 | 25.24 |
| PROLINE | 18.625 | 18.625 | 18.625 | 18.625 | 18.625 | 18.625 | 18.625 | 18.625 | 18.625 | 18.625 | 18.625 | 18.625 |
| SERINE | 28.125 | 28.125 | 28.125 | 28.125 | 28.125 | 28.125 | 28.125 | 28.125 | 28.125 | 28.125 | 28.125 | 28.125 |
| THREONINE | 36.725 | 36.725 | 36.725 | 36.725 | 36.725 | 36.725 | 36.725 | 36.725 | 36.725 | 36.725 | 36.725 | 36.725 |
| TRYPTOPHAN | 7.01 | 7.01 | 7.01 | 7.01 | 7.01 | 7.01 | 7.01 | 7.01 | 7.01 | 7.01 | 7.01 | 7.01 |
| TYROSINE 2Na·H₂O | 42.31 | 42.31 | 42.31 | 42.31 | 42.31 | 42.31 | 42.31 | 42.31 | 42.31 | 42.31 | 42.31 | 42.31 |
| VALINE | 36.425 | 36.425 | 36.425 | 36.425 | 36.425 | 36.425 | 36.425 | 36.425 | 36.425 | 36.425 | 36.425 | 36.425 |

| AMINO ACID CONTENT (mg/L) | CONVENTIONAL DIET | AMINO ACID COMPOSITION IN MEDIUM | | | | | | | | | |
|---|---|---|---|---|---|---|---|---|---|---|---|
| | | N(-Asn) | P(-Pro) | Q(-Gln) | R(-Arg) | S(-Ser) | T(-Thr) | V(-Val) | W(-Trp) | Y(-Tyr) | -All |
| ALANINE | 2.225 | 2.225 | 2.225 | 2.225 | 2.225 | 2.225 | 2.225 | 2.225 | 2.225 | 2.225 | 0 |
| ARGININE HCl | 73.75 | 73.75 | 73.75 | 73.75 | 0 | 73.75 | 73.75 | 73.75 | 73.75 | 73.75 | 0 |
| ARGININE | 100 | 100 | 100 | 100 | 0 | 100 | 100 | 100 | 100 | 100 | 0 |
| ANHYDROUS ASPARAGINE | 25 | 0 | 25 | 25 | 25 | 25 | 25 | 25 | 25 | 25 | 0 |
| ASPARAGINE H₂O | 3.75 | 0 | 3.75 | 3.75 | 3.75 | 3.75 | 3.75 | 3.75 | 3.75 | 3.75 | 0 |
| ASPARTIC ACID | 13.325 | 13.325 | 13.325 | 13.325 | 13.325 | 13.325 | 13.325 | 13.325 | 13.325 | 13.325 | 0 |
| CYSTEINE 2HCl | 48.245 | 48.245 | 48.245 | 48.245 | 48.245 | 48.245 | 48.245 | 48.245 | 48.245 | 48.245 | 0 |
| CYSTEINE HCl·H₂O | 8.78 | 8.78 | 8.78 | 8.78 | 8.78 | 8.78 | 8.78 | 8.78 | 8.78 | 8.78 | 0 |
| GLUTAMIC ACID | 13.675 | 13.675 | 13.675 | 13.675 | 13.675 | 13.675 | 13.675 | 13.675 | 13.675 | 13.675 | 0 |
| GLUTAMINE | 332.5 | 332.5 | 332.5 | 0 | 332.5 | 332.5 | 332.5 | 332.5 | 332.5 | 332.5 | 0 |
| GLYCINE | 14.375 | 14.375 | 14.375 | 14.375 | 14.375 | 14.375 | 14.375 | 14.375 | 14.375 | 14.375 | 0 |
| HISTIDINE HCl·H2O | 15.74 | 15.74 | 15.74 | 15.74 | 15.74 | 15.74 | 15.74 | 15.74 | 15.74 | 15.74 | 0 |
| HISTIDINE | 7.5 | 7.5 | 7.5 | 7.5 | 7.5 | 7.5 | 7.5 | 7.5 | 7.5 | 7.5 | 0 |
| HYDROXYPROLINE | 10 | 10 | 0 | 10 | 10 | 10 | 10 | 10 | 10 | 10 | 0 |
| ISOLEUCINE | 297.35 | 297.35 | 297.35 | 297.35 | 297.35 | 297.35 | 297.35 | 297.35 | 297.35 | 297.35 | 0 |
| LEUCINE | 54.525 | 54.525 | 54.525 | 54.525 | 54.525 | 54.525 | 54.525 | 54.525 | 54.525 | 54.525 | 0 |
| LYSINE HCl | 65.625 | 65.625 | 65.625 | 65.625 | 65.625 | 65.625 | 65.625 | 65.625 | 65.625 | 65.625 | 0 |
| METHIONINE | 16.12 | 16.12 | 16.12 | 16.12 | 16.12 | 16.12 | 16.12 | 16.12 | 16.12 | 16.12 | 0 |
| PHENYLALANINE | 25.24 | 25.24 | 25.24 | 25.24 | 25.24 | 25.24 | 25.24 | 25.24 | 25.24 | 25.24 | 0 |
| PROLINE | 18.625 | 18.625 | 0 | 18.625 | 18.625 | 18.625 | 18.625 | 18.625 | 18.625 | 18.625 | 0 |
| SERINE | 28.125 | 28.125 | 28.125 | 28.125 | 28.125 | 0 | 28.125 | 28.125 | 28.125 | 28.125 | 0 |
| THREONINE | 36.725 | 36.725 | 36.725 | 36.725 | 36.725 | 36.725 | 0 | 36.725 | 36.725 | 36.725 | 0 |
| TRYPTOPHAN | 7.01 | 7.01 | 7.01 | 7.01 | 7.01 | 7.01 | 7.01 | 7.01 | 0 | 7.01 | 0 |
| TYROSINE 2Na·H₂O | 42.31 | 42.31 | 42.31 | 42.31 | 42.31 | 42.31 | 42.31 | 42.31 | 42.31 | 0 | 0 |
| VALINE | 36.425 | 36.425 | 36.425 | 36.425 | 36.425 | 36.425 | 36.425 | 0 | 36.425 | 36.425 | 0 |

FIG. 1

A
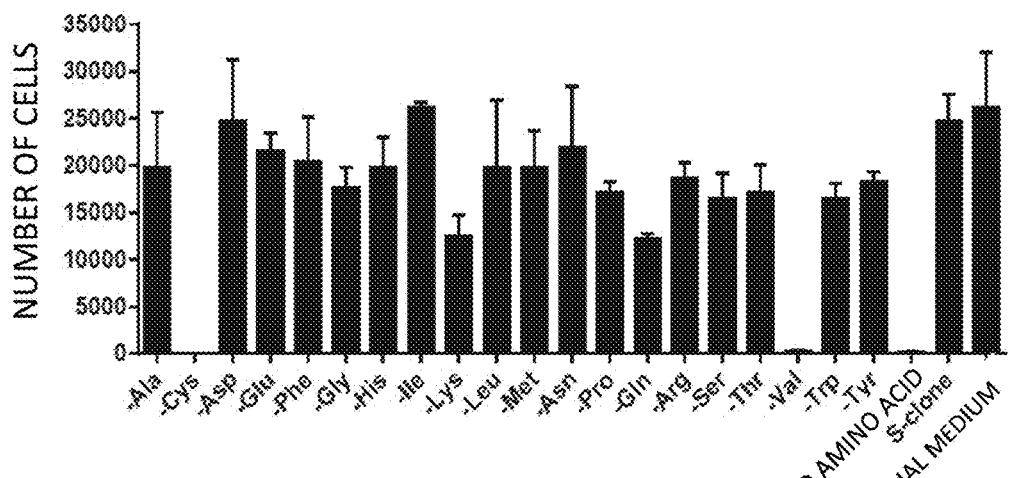
B
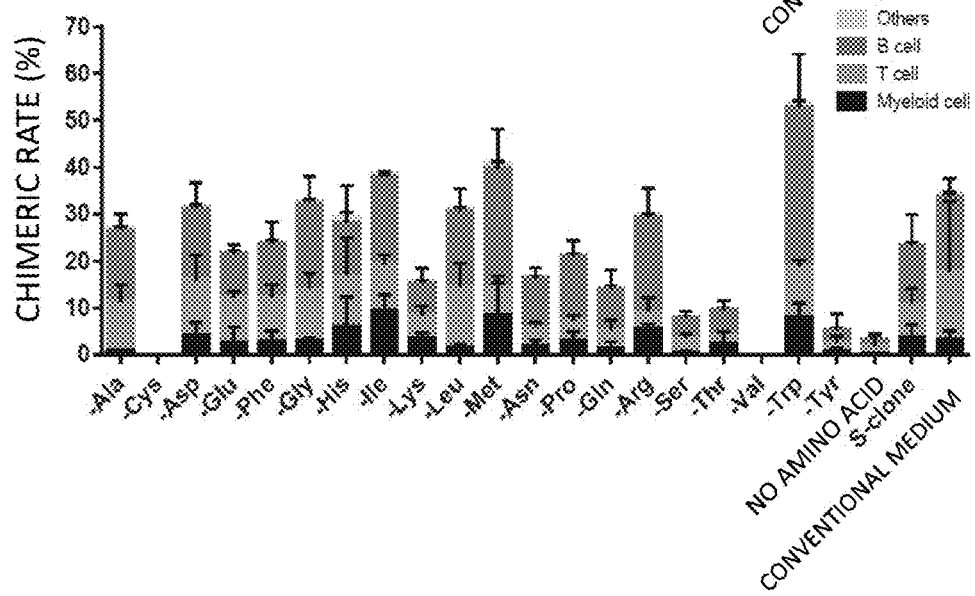
FIG. 3

| PRODUCT NUMBER | A10021B CONVENTIONAL DIET | | A05080209 −Val | | A05080217 −Cys | |
|---|---|---|---|---|---|---|
| | gm % | kcal % | gm % | kcal % | gm % | kcal % |
| PROTEIN | 17 | 18 | 16 | 17 | 17 | 17 |
| CARBOHYDRATE | 69 | 71 | 69 | 72 | 69 | 71 |
| LIPID | 5 | 12 | 5 | 12 | 5 | 12 |
| total | | 100 | | 100 | | 100 |
| kcal/gm | 3.9 | | 3.9 | | 3.9 | |
| CONSTITUENT (gm) | | | | | | |
| L-Arginine | 10 | 40 | 10 | 40 | 10 | 40 |
| L-Histidine-HCl-H2O | 6 | 24 | 6 | 24 | 6 | 24 |
| L-Isoleucine | 8 | 32 | 8 | 32 | 8 | 32 |
| L-Leucine | 12 | 48 | 12 | 48 | 12 | 48 |
| L-Lysine-HCl | 14 | 56 | 14 | 56 | 14 | 56 |
| L-Methionine | 6 | 24 | 6 | 24 | 6 | 24 |
| L-Phenylalanine | 8 | 32 | 8 | 32 | 8 | 32 |
| L-Threonine | 8 | 32 | 8 | 32 | 8 | 32 |
| L-Tryptophan | 2 | 8 | 2 | 8 | 2 | 8 |
| L-Valine | 8 | 32 | 0 | 0 | 8 | 32 |
| L-Alanine | 10 | 40 | 10 | 40 | 10 | 40 |
| L-Asparagine-H2O | 5 | 20 | 5 | 20 | 5 | 20 |
| L-Aspartate | 10 | 40 | 10 | 40 | 10 | 40 |
| L-Cystine | 4 | 16 | 4 | 16 | 0 | 0 |
| L-Glutamic Acid | 30 | 120 | 30 | 120 | 30 | 120 |
| L-Glutamine | 5 | 20 | 5 | 20 | 5 | 20 |
| Glycine | 10 | 40 | 10 | 40 | 10 | 40 |
| L-Proline | 5 | 20 | 5 | 20 | 5 | 20 |
| L-Serine | 5 | 20 | 5 | 20 | 5 | 20 |
| L-Tyrosine | 4 | 16 | 4 | 16 | 4 | 16 |
| Total L-Amino Acids | 170 | 680 | 162 | 648 | 166 | 664 |
| CORN STARCH | 550.5 | 2202 | 558.5 | 2234 | 554.5 | 2218 |
| MALTODEXTRIN 10 | 125 | 500 | 125 | 500 | 125 | 500 |
| SUCROSE | 0 | 0 | 0 | 0 | 0 | 0 |
| CELLULOSE | 50 | 0 | 50 | 0 | 50 | 0 |
| CORN OIL | 50 | 450 | 50 | 450 | 50 | 450 |
| Mineral Mix S10001 | 35 | 0 | 35 | 0 | 35 | 0 |
| SODIUM HYDROGEN CARBONATE | 7.5 | 0 | 7.5 | 0 | 7.5 | 0 |
| Vitamin Mix V10001 | 10 | 40 | 10 | 40 | 10 | 40 |
| CHOLINE BITARTRATE | 2 | 0 | 2 | 0 | 2 | 0 |
| DYE | | | | | | |
| Yellow Dye, FD&C #5 | 0 | 0 | 0 | 0 | 0.01 | 0 |
| Red Dye, FD&C #4 | 0 | 0 | 0.025 | 0 | 0 | 0 |
| Blue Dye, FD&C #1 | 0.05 | 0 | 0.025 | 0 | 0.04 | 0 |
| Total | 1000.05 | 3872 | 1000.05 | 3872 | 1000.05 | 3872 |

FIG. 4

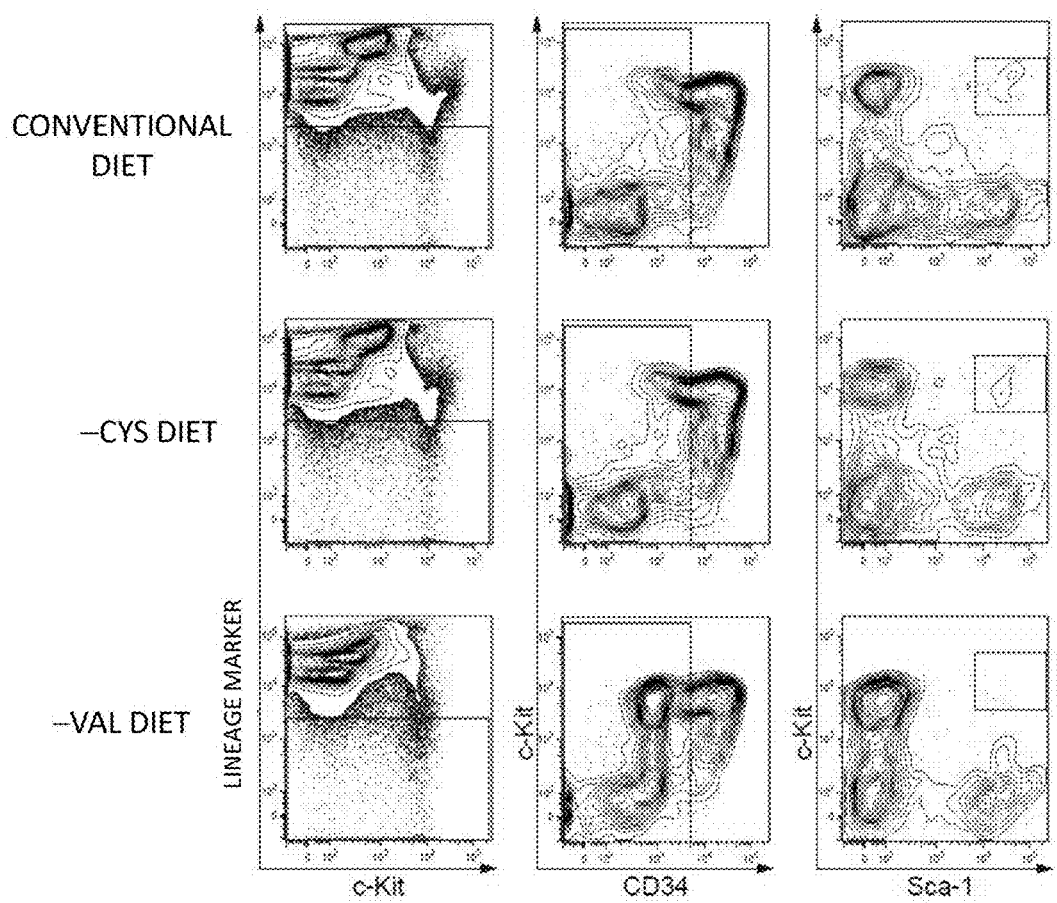
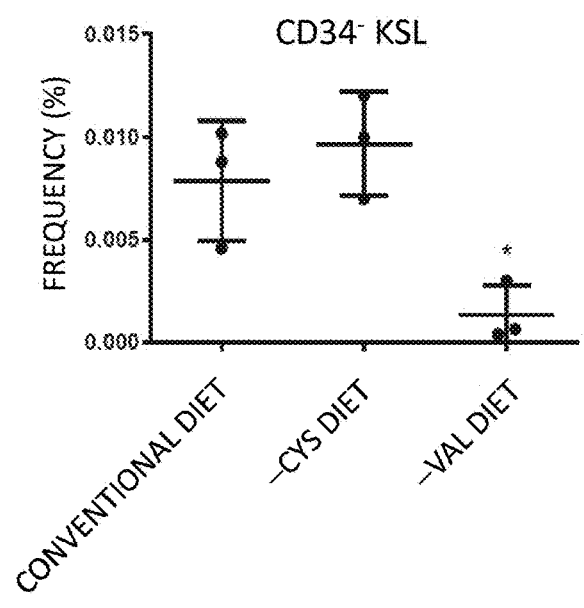
FIG. 8

A
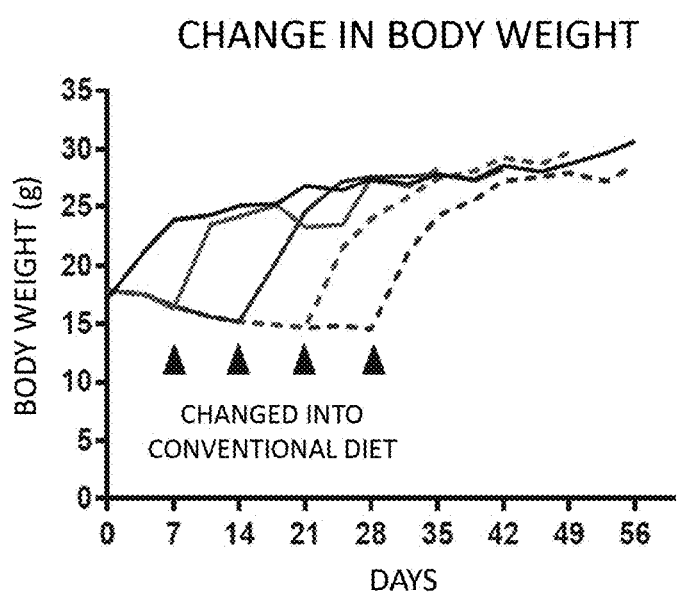
B
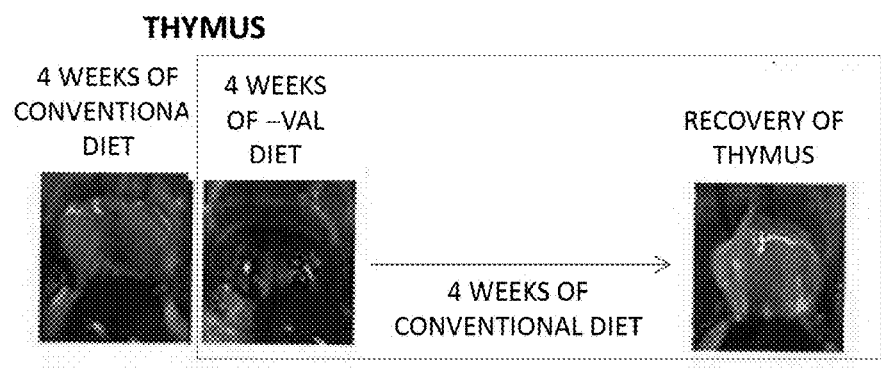
C
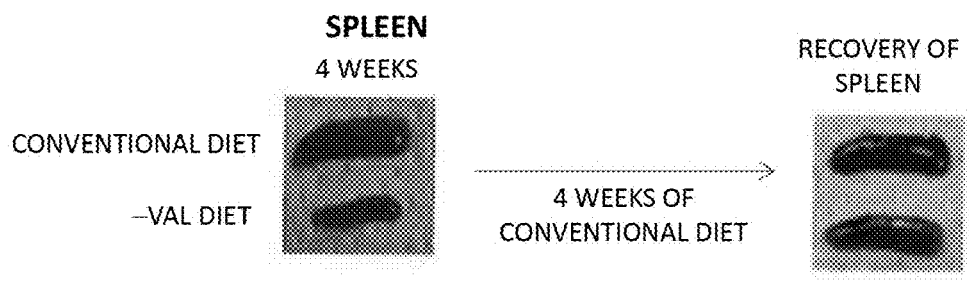
FIG. 11

A
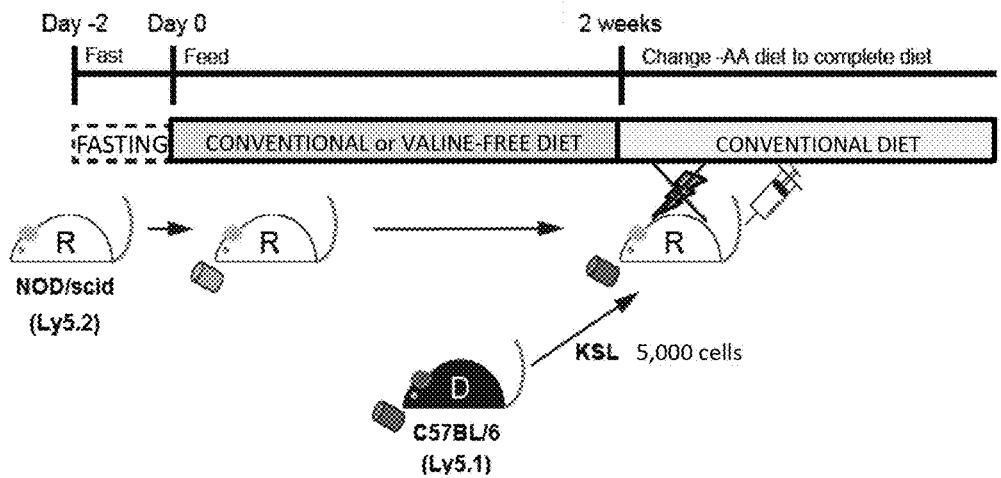
B
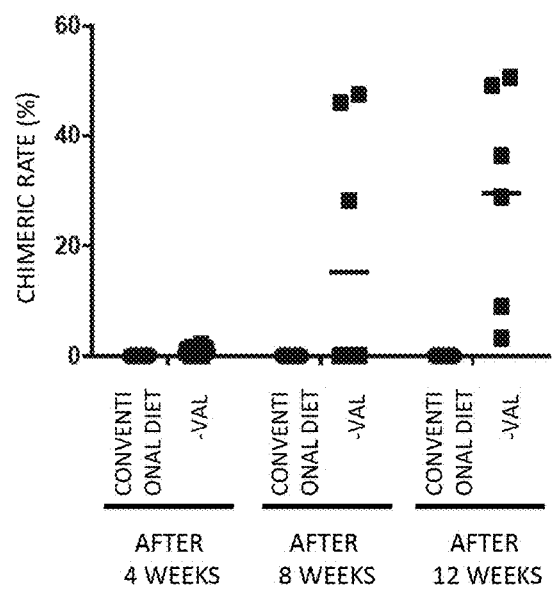
C
| | CONVENTIONAL DIET | −VAL DIET |
|---|---|---|
| SUCCESS IN TRANSPLANTATION | 0/10 | 6/6 |
| DEATH | 0/10 | 4/10 |
| CHIMERIC RATE | 0 | 29.5 ± 20.0% |
| BONE MARROW CELL | 0 | 22.0 ± 2.95% |
| T CELL | 0 | 26.2 ± 2.24% |
| B CELL | 0 | 47.9 ± 2.43% |
FIG. 14

COMPOSITION FOR DECREASING HEMATOPOIETIC STEM CELLS, AND METHOD FOR PRODUCING SAME

TECHNICAL FIELD

The present invention relates to a composition and a medium for decreasing hematopoietic stem cells and a method for producing the same.

BACKGROUND ART

Attempts have actively been made in recent years for therapy of hematopoietic cell disease by hematopoietic stem cell transplantation. The hematopoietic stem cell transplantation requires treatment for eliminating a patient's hematopoietic stem cells. Examples of the treatment for eliminating hematopoietic stem cells include radiation exposure and chemotherapy to the patient; however, these treatments have strong side effects and result in great burden for the patient. This is prominent particularly when the patient undergoing hematopoietic cell transplantation is an old person or a child. However, no useful method for eliminating hematopoietic stem cells is known other than radiation exposure and chemotherapy.

In mice fed on a protein-free diet, severe agranulocytosis and anemia are known to occur (Non Patent Literature 1). These abnormalities of blood cells were recovered using 18% casein and folic acid (Non Patent Literature 1).

CITATION LIST

Non Patent Literature

Non Patent Literature 1

Kornberg A, Daft F S, Sebrell W H, Granulocytopenia and Anemia in Rats Fed Diets of Low Casein Content, Science, 1949, 103(2682): 646-8.

SUMMARY OF INVENTION

Technical Problem

The present invention provides a technique replacing radiation exposure in decreasing or eliminating hematopoietic stem cells in an animal (particularly human) body.

Solution to Problem

The present inventors have found that as described in Examples below, the maintenance of animals without giving valine can decrease hematopoietic stem cells in the animal bodies. The phenomenon that hematopoietic stem cells are decreased has been a phenomenon characteristic of the hematopoietic stem cells to the extent that it is observed.

The inventors have further found that when hematopoietic stem cells are transplanted into animals in which hematopoietic stem cells are decreased by maintenance without giving valine (referred to as "recipient animals"), the transplanted hematopoietic stem cells are engrafted in the recipient animal bodies. When hematopoietic stem cells in the recipient animal bodies are examined in detail, no contribution of cells derived from the recipient animals to the hematopoietic system is identified and the hematopoietic stem cells have been found to be replaced by the transplanted hematopoietic stem cells. From this, it has been found that the method of the present invention can be applied to the treatment of recipients before hematopoietic stem cell transplantation.

The present invention has been made based on these findings.

Thus, according to the present application invention, the following inventions are provided.

(1) A parenteral nutrition formula or an enteral nutrition formula, wherein the formula is substantially free of valine.

(2) A composition for use in decreasing hematopoietic stem cells, wherein the composition comprises the nutrition formula according to (1) above and is substantially free of valine.

(3) A composition for use in decreasing hematopoietic stem cells, wherein the composition has a composition which is the same as parenteral nutrition formula or enteral nutrition formula except for valine and is substantially free of valine.

(4) The composition according to (2) or (3) above, wherein a subject for administration is a recipient before hematopoietic stem cell transplantation.

(5) The composition according to any one of (2) to (4) above, wherein the parenteral nutrition formula or the enteral nutrition formula is designed to enable the supply of nutrients sufficient for at least 3 weeks of life support by successive administration except for being substantially free of valine.

(6) The composition according to any one of (2) to (5) above, wherein the parenteral nutrition formula or the enteral nutrition formula is designed as a complete nutrition formulation except for being substantially free of valine.

(7) The composition according to any one of (2) to (6) above for parenteral administration.

(8) A cell culture medium, wherein the medium is substantially free of valine or cysteine or both.

(9) A method for detecting a decrease in hematopoietic stem cells in a subject's body, the method comprising the steps of:

(a) counting the number of hematopoietic stem cells in a bone marrow fluid or peripheral blood sample obtained from a recipient before treatment;

(b) counting the number of hematopoietic stem cells in a bone marrow fluid or peripheral blood sample obtained from the recipient during the treatment or after the treatment; and (c) comparing the number of the cells determined in the step (a) and the number of the cells obtained in the step (b), wherein the treatment gives substantially no valine to the recipient during a certain period of time.

(10) The method according to (9) above, wherein the treatment is carried out by administering the nutrition formula according to (1) above or the composition according to any one of (2) to (7) above.

(11) The method according to (9) above, wherein the treatment is a nutrition therapy characterized by giving substantially no valine to the subject during a certain period of time.

(12) A method for producing a composition for use in decreasing hematopoietic stem cells, the method comprising mixing nutrients essential for a living body in such a way that the composition is substantially free of valine.

(13) The method according to (12) above, wherein the nutrients are at least sugar, essential amino acids, vitamins, and essential trace elements.

(14) The method according to (12) above, wherein the composition comprises a sufficient amount of nutrients for at least 3 weeks of life support by successive administration.

(15) Use of nutrients for the manufacture of a pharmaceutical composition for use in decreasing hematopoietic stem cells, wherein the nutrients are nutrients other than valine.

According to the present invention, hematopoietic stem cells can be decreased by simply culturing the hematopoietic stem cells in a valine- or cysteine-free medium. The invention is advantageous in being high in cell specificity and capable of targeting stem cells with high specificity. According to the present invention, hematopoietic stem cells can also be decreased in a subject (for example, a human) by giving a valine-free food. The invention is advantageous in not requiring, or being capable of reducing, conventional radiation exposure.

BRIEF DESCRIPTION OF DRAWINGS

FIG. 1 shows the content of amino acids in a cell culture medium.

FIG. 3A shows the number of cells counted after seeding CD34-KSL cells in an amount of 40 cells per well and culturing the cells for 1 week in a medium having the composition shown in FIG. 1. FIG. 3B shows the chimeric rate when cells obtained by seeding CD34-KSL cells in an amount of 40 cells per well were transplanted into irradiated mice in conditions competitive with normal cells.

FIG. 4 shows the compositions of a normal diet, a valine-free diet, and a cysteine-free diet.

FIG. 8 shows the existence frequency of $CD34^-$KSL cells in the bone marrow of mice fed on a normal diet, a valine-free diet (−Val), or a cysteine-free diet (−Cys) for 4 weeks.

FIG. 11A shows the transition of a change in the body weight of mice given a valine-free diet and then a normal diet in place thereof. FIGS. 11B and 11C show that the thymus became smaller in a mouse fed on a valine-free diet for 4 weeks and then recovered in size by feeding the mice on a normal diet for 4 weeks.

FIG. 14A shows the scheme of hematopoietic stem cell transplantation. In this scheme, recipient mice are not irradiated and receive donor cell transplantation after being fed on a valine-free diet for 2 weeks. FIG. 14B shows the chimeric rate of donor cells in the recipients after transplantation. FIG. 14C shows the success rate of transplantation and the contribution rate of donor cells in the recipients after transplantation for each type of cells.

DESCRIPTION OF EMBODIMENTS

Figure 2:
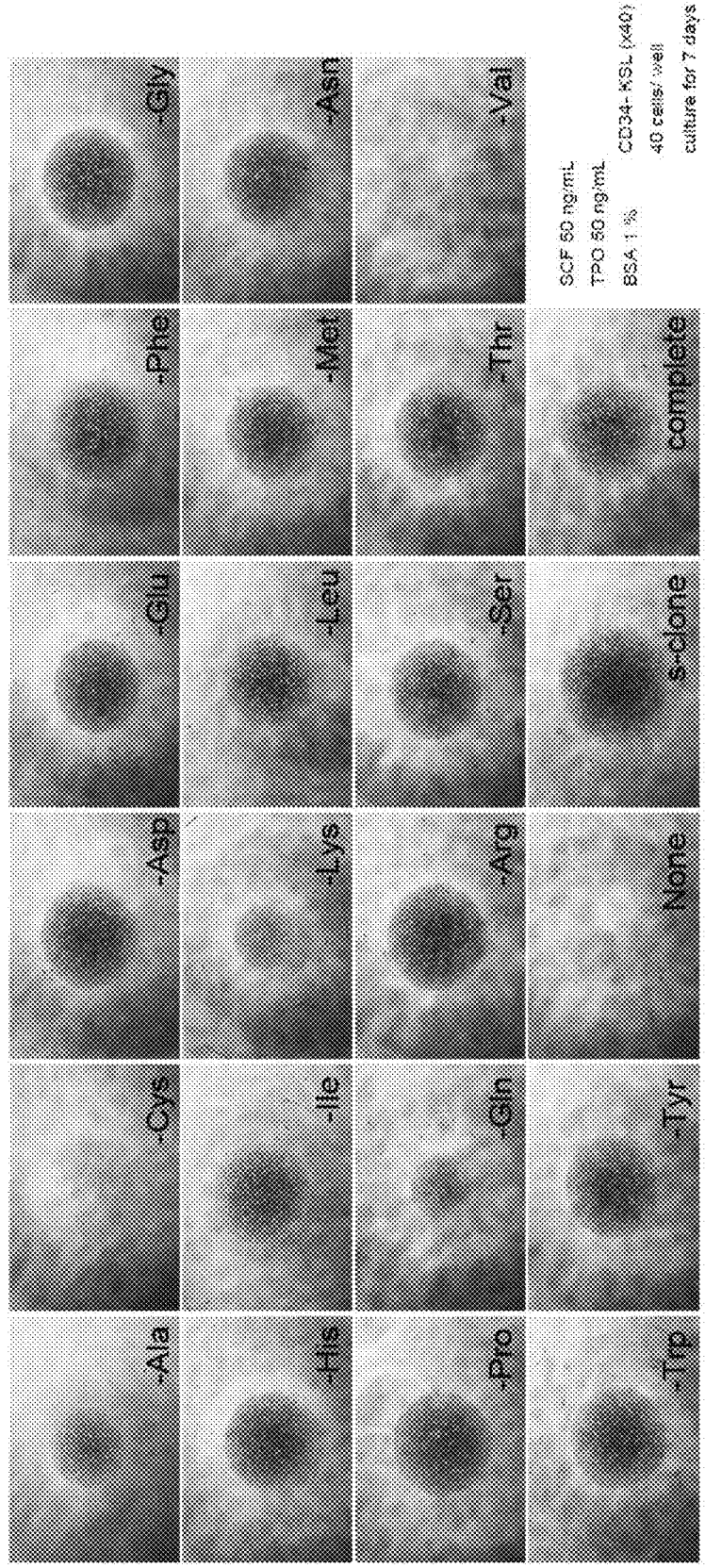
FIG. 2 shows the results of seeding CD34-KSL cells in an amount of 40 cells per well and culturing the cells for 1 week in a medium having the composition shown in FIG. 1.

The present inventors have found that the maintenance of animals without giving valine can decrease hematopoietic stem cells in the animal bodies as described in Examples below. Thus, according to the present invention, a method for decreasing hematopoietic stem cells in an animal body by maintaining the animal without giving valine, and a composition used for the method are provided.

According to the present invention, the subject can be nutriently managed so that valine is not given to the subject. This decreases hematopoietic stem cells in the subject's body. The extension of the period of the nutrient management can substantially completely eliminate hematopoietic stem cells from the subject's body. Eliminating cells substantially completely means that the cells are lost to 10% or less, more preferably 5% or less, yet more preferably 3% or less, yet more preferably 1% or less, yet more preferably 0.1% or less, particularly preferably 0.01% or less, most preferably completely.

In an aspect, the composition for use in decreasing hematopoietic stem cells comprises a parenteral nutrition formulation or an enteral nutrition formulation; however, the parenteral nutrition formulation or the enteral nutrition formulation is a composition substantially free of valine. As used herein, "free of valine" is used interchangeably with "lacking valine". As used herein, the "free of valine" means also free of valine in the form of a peptide. As used herein, "substantially" means that there may be contamination to the extent unavoidable in a production process.

The "parenteral nutrition formulation" here means a nutrition formula used for the parenteral nutrition method. Examples of the parenteral nutrition formulation include a peripheral vein nutrition formulation for which nutrients are administered into a peripheral vein and a central vein nutrition formulation for which nutrients are administered into the central vein. Typically, when the bowel functions, the enteral nutrition method is chosen as a nutrition method and an enteral nutrition formulation is administered to a subject; however, when enteral nutrition is difficult, the parenteral nutrition method is chosen and parenteral nutrition formulation is administered to the subject. Examples of the parenteral nutrition formulation include a peripheral intravenous nutrition formulation and a central intravenous nutrition formulation. The parenteral nutrition formulation is typically a transfusion formulation, is an aqueous solution containing sugars, electrolytes, and amino acids, and may further contain vitamins. The total parenteral nutrition formulation typically contains vitamins and trace elements necessary for a living body (for example, a vitamin preparation for transfusion, a multivitamin preparation for transfusion, and a trace element formulation for transfusion) in addition to sugars, electrolytes, and amino acids.

The "enteral nutrition formulation" means a nutrition formula used for the enteral nutrition method. Examples of the enteral nutrition formulation include a semi-digestion nutrition agent, a digestion nutrition agent, and a component nutrition agent. The semi-digestion nutrition agent contains protein as a nitrogen source; the digestion nutrition agent contains small peptides and amino acids as nitrogen sources; and the component nutrition agent contains amino acids as a nitrogen source. According to the present invention, the component nutrition agent can be preferably used as the enteral nutrition formulation.

As used herein, the "having a composition as parenteral nutrition formulation or enteral nutrition formulation except for valine" means that the composition except valine is the same as that of the parenteral nutrition formulation or the enteral nutrition formulation or similar thereto and has a function as the parenteral nutrition formulation or the enteral nutrition formulation.

As used herein, "designed as a complete nutrition formulation except for being substantially free of valine" means having the composition of the nutrient formulation designed as a complete nutrition formulation but containing no valine in the composition. In other words, for the composition "designed as a complete nutrition formulation except for being substantially free of valine", the composition except valine can be the same as that of the complete nutrition formulation.

As used herein, "designed to enable the supply of nutrients sufficient for at least 3 weeks of life support by successive administration except for being substantially free of valine" or similar expression means having the composition of the nutrient formulation designed to enable the supply of nutrients sufficient for at least 3 weeks of life support by successive administration but containing no valine in the composition.

The parenteral nutrition method or the enteral nutrition method may be chosen as a nutritional management method so that the nutritional management of a subject is medically properly carried out. The parenteral nutrition formulation or the enteral nutrition formulation is marketed for such proper nutritional management. In the parenteral nutrition method or the enteral nutrition method, a formulation increasing energy intake, such as a fat emulsion preparation, may be combined in addition to the parenteral nutrition formulation or the enteral nutrition formulation. The fat emulsion preparation is administered in combination with the nutrient formulation for energy supply or for prevention of fatty acid deficiency, and typically contains an emulsified product of fatty acid; the fatty acid can be derived from, for example, soybean oil and the emulsifying agent can be, for example, lecithin derived from egg yolk.

According to the present invention, the maintenance of an animal without giving valine can decrease hematopoietic stem cells in the body of the subject animal, and, therefore, the parenteral nutrition formulation or the enteral nutrition formulation substantially free of valine can preferably be used to decrease hematopoietic stem cells.

The composition for use in decreasing hematopoietic stem cells according to the present invention is designed so that its successive administration can supply sufficient nutrients for the survival of a recipient at least beyond a period until subject-derived hematopoietic stem cells decrease preferably to 10% or less, more preferably 5% or less, still more preferably 3% or less, yet more preferably 1% or less of those before administration and most preferably completely disappear. On this occasion, the composition may be combined with a formulation increasing energy intake, such as a fat emulsion preparation.

Thus, the composition for use in decreasing hematopoietic stem cells according to the present invention can be administered to a subject to decrease subject-derived hematopoietic stem cells preferably to 10% or less, more preferably 5% or less, still more preferably 3% or less, yet more preferably 1% or less of those before administration, or most preferably to completely lose the cells.

In an aspect, the composition for use in decreasing hematopoietic stem cells according to the present invention contains all amino acids other than valine of 20 amino acids. In an aspect, the composition for use in decreasing hematopoietic stem cells according to the present invention is substantially free of a peptide containing valine. In an aspect, the composition for use in decreasing hematopoietic stem cells according to the present invention contains all amino acids other than valine of the 20 amino acids and further contains sugars, electrolytes, vitamins, and essential trace elements. In an aspect, the composition for use in decreasing hematopoietic stem cells according to the present invention contains all amino acids other than valine of 20 amino acids and further contains sugars, electrolytes, vitamins, and essential trace elements; and the composition is used in combination with a fat emulsion preparation. The amount of each component contained in the composition for use in decreasing hematopoietic stem cells according to the present invention may be comparable to the amount of each component contained in a conventional parenteral nutrition formula or enteral nutrition formula.

According to the present invention, the subject is a mammal, preferably a human. In an aspect, the subject for administration of the composition of the present invention is a patient with hematopoietic tumor. Thus, in an aspect, the composition of the present invention is a pharmaceutical composition for treating hematopoietic tumor in a patient with hematopoietic tumor. In a preferred aspect, the hematopoietic tumor is a hematopoietic tumor involving hematopoietic cancer stem cells.

In the pharmaceutical composition for intravenous administration, each nutrient consists of a pharmaceutically acceptable component.

In an aspect of the present invention, the subject for administration of the composition of the present invention is a recipient before hematopoietic stem cell transplantation. For the recipient of hematopoietic stem cell transplantation, who has a nutritional risk, nutritional management, such as using the intravenous nutrition method or the enteral nutrition method, is recommended irrespective of the presence or absence of nutritional disturbance. The parenteral nutrition formulation or enteral nutrition formulation used for the nutritional management of a recipient of hematopoietic stem cell transplantation is also well known. Thus, the composition for use in decreasing hematopoietic stem cells according to the present invention may be a conventional parenteral nutrition formulation or enteral nutrition formulation used for the nutritional management of a recipient before hematopoietic stem cell transplantation (provided that, the nutrient formulations are free of valine). The parenteral nutrition formulation or enteral nutrition formulation used for the nutritional management of a recipient of hematopoietic stem cell transplantation can be one in which the amount of energy or the amount of protein is increased compared to that of conventionally used formulation.

The amount of energy administration using the nutrition formula can be measured by a technique well-known to those skilled in the art, for example, by indirect calorimetry.

The parenteral nutrition formulation or enteral nutrition formulation substantially free of valine can be obtained by mixing an amino acid preparation other than valine as amino acids with other constituents of the nutrition formula (sugars, electrolytes, and the like).

The composition for use in decreasing hematopoietic stem cells according to the present invention may be one designed to enable the supply of nutrients sufficient for at least 3 weeks of life support by successive administration, preferably one designed to enable the supply of nutrients sufficient for 4 weeks or 5 weeks or more of life support.

In an aspect, the composition for use in decreasing hematopoietic stem cells according to the present invention can be a composition for use in substantially completely eliminating hematopoietic stem cells from a subject's body.

According to the present invention, giving substantially no valine but the other nutrients to a subject decreases hematopoietic stem cells in the subject's body. Thus, according to the present invention, provided is a method for decreasing hematopoietic stem cells in a subject's body, the method comprising nutritionally managing (nourishing) a subject so that valine is not substantially given. The nutritional management can be carried out by the enteral nutrition method or the parenteral nutrition method. The nutritional management may be carried out by administering the parenteral nutrition formulation or the enteral nutrition formulation to a subject.

The subject is a mammal, preferably a human.

The composition for use in decreasing hematopoietic stem cells according to the present invention is also a composition for use in suppressing the division of hematopoietic stem cells.

According to the present invention, is provided a method for detecting a decrease in hematopoietic stem cells in a subject's body, the method comprising the steps of:

(a) counting the number of hematopoietic stem cells in a bone marrow fluid or peripheral blood sample obtained from a subject before treatment;

(b) counting the number of hematopoietic stem cells in a bone marrow fluid or peripheral blood sample obtained from the subject during the treatment or after the treatment; and (c) comparing the number of the cells determined in the step (a) and the number of the cells obtained in the step (b), wherein the treatment gives substantially no valine to the subject during a certain period of time. For this method, the number of the cells obtained in step (b) being smaller than the number of the cells determined in step (a) in step (c) can be determined as a decrease in the hematopoietic stem cells in the body. In an aspect, the treatment is a nutrition therapy using the enteral nutrition method or the parenteral nutrition method. In an aspect, the treatment may be carried out by administering the parenteral nutrition formulation or the enteral nutrition formulation to a subject.

For the method for detecting a decrease in hematopoietic stem cells in a subject's body according to the present invention, the certain period of time is preferably 1 day or more, 2 days or more, 3 days or more, 4 days or more, 5 days or more, 6 days or more, 1 week or more, 2 weeks or more, 3 weeks or more, or 4 weeks or more, and should not be a period long enough for a patient to die. In an aspect of the present invention, the certain period of time approximately ranges 1 day to 5 weeks, 1 week to 4 weeks, or 2 weeks to 3 weeks.

For the method for detecting a decrease in hematopoietic stem cells in a subject's body according to the present invention, the subject may be a mammal, preferably a human. In an aspect of the present invention, the subject is a recipient before hematopoietic stem cell transplantation. In an aspect of the present invention, the subject is a patient with hematopoietic tumor.

According to the present invention, provided is a method for producing a composition for use in decreasing hematopoietic stem cells, the method comprising mixing nutrients in such a way that the composition substantially free of valine. The mixed nutrients can be sugars, amino acids, vitamins, electrolytes, and essential trace elements. In an aspect, the mixed amino acids are one or more amino acids or all amino acids selected from the essential amino acids, such as tryptophan, lysine, methionine, phenylalanine, threonine, leucine, isoleucine, and histidine. The composition administered by the parenteral nutrition method consists of pharmaceutically acceptable components.

Examples of the trace element necessary in the body include iron, zinc, copper, selenium, chromium, cobalt, iodine, manganese, and molybdenum. The dosage of the trace elements is roughly as follows.

Iron: 20 to 200 μg/kg body weight/day
Zinc: 40 to 60 μg/kg body weight/day
Copper: 20 to 50 μg/kg body weight/day
Selenium: 2 to 7 μg/kg body weight/day
Chromium: 0.1 to 0.2 μg/kg body weight/day
Iodine: 1 to 15 μg/kg body weight/day
Manganese: 1 to 60 μg/kg body weight/day
Molybdenum: 0.1 to 0.5 μg/kg body weight/day Thus, essential trace elements can be mixed in the composition of the present invention using the above necessary amounts as a guide.

According to the present invention, provided is a method for transplanting hematopoietic stem cells, comprising maintaining the life of a recipient of transplantation without substantially giving valine (that is, by giving the other nutrients) to the subject during a certain period of time and thereby decreasing hematopoietic stem cells in the patient's body. The method for transplanting hematopoietic stem cells according to the present invention may further comprise giving substantially no valine to the subject until patient's hematopoietic stem cells are substantially eliminated and, after the elimination, transplanting hematopoietic stem cells.

According to the present invention, provided is a method for treating hematopoietic tumor in a patient in need thereof, the method comprising maintaining the life of a patient without substantially giving valine (that is, by giving the other nutrients) to the subject during a certain period of time and thereby decreasing hematopoietic stem cells in the patient's body. The method for treating hematopoietic tumor according to the present invention may be carried out before, after, or during therapy with an anticancer agent used for hematopoietic tumor treatment. The method for treating hematopoietic tumor according to the present invention may further comprise giving substantially no valine to the subject until patient's hematopoietic stem cells are substantially eliminated and, after the elimination, transplanting hematopoietic stem cells. The method for treating hematopoietic tumor according to the present invention exerts an extremely high effect in treating hematopoietic tumor particularly in terms of being capable of decreasing the amount of cancer stem cells responsible for hematogenesis.

The present invention relates to the use of nutrients for producing a pharmaceutical composition for use in decreasing hematopoietic stem cells, the nutrients being nutrients other than valine. The nutrients used can be sugars, amino acids, vitamins, electrolytes, and essential trace elements. In an aspect, the amino acids used are one or more amino acids selected from the group consisting of essential amino acids, such as tryptophan, lysine, methionine, phenylalanine, threonine, leucine, isoleucine, and histidine, or all amino acids selected from the group consisting of the essential amino acids. In an aspect, the nutrients include all of the amino acids other than valine as amino acids.

In an aspect, the amino acids used are all amino acids (excluding valine). Thus, in an aspect, the nutrients used are sugars, amino acids, vitamins, electrolytes, and essential trace elements, wherein the amino acid is one or more amino acids selected from the group consisting of essential amino acids, such as tryptophan, lysine, methionine, phenylalanine, threonine, leucine, isoleucine, and histidine, or all amino acids selected from the group consisting of the essential amino acids.

In an aspect, the nutrients used are sugars, amino acids, vitamins, electrolytes, and essential trace elements, wherein the amino acids are asparagine, aspartic acid, serine, threonine, glutamine, glutamic acid, proline, glycine, methionine, leucine, isoleucine, tyrosine, phenylalanine, histidine, alanine, lysine, tryptophan, and arginine.

In an aspect, the nutrients used are sugars, amino acids, vitamins, electrolytes, and essential trace elements, wherein the amino acids are asparagine, aspartic acid, serine, threonine, glutamine, glutamic acid, proline, glycine, methionine, leucine, isoleucine, tyrosine, phenylalanine, histidine, alanine, lysine, tryptophan, cysteine, and arginine.

The content of each nutrient used can be properly determined by those skilled in the art depending on the subject given administration. For example, the content of each nutrient used may be equivalent to the content of each nutrient in the parenteral nutrition formula or the enteral nutrition formula.

In an aspect of the present invention, a cell culture medium for use in decreasing hematopoietic stem cells is provided. The cell culture medium of the present invention is characterized by being substantially free of valine or cysteine or both. In an aspect, the cell culture medium of the present invention has the same composition as a conventional cell culture medium except for being substantially free of valine or cysteine or both. For example, the conventional cell culture medium is a synthetic medium (complete synthetic medium). Thus, in an aspect, the cell culture medium of the present invention is a complete synthetic medium substantially free of valine or cysteine or both. Those skilled in the art can properly determine the composition of the complete synthetic medium. The content of each component may be equivalent to that of a conventionally used complete synthetic medium. The cell culture medium of the present invention can be used, for example, for eliminating undifferentiated cells (hematopoietic stem cells) from a differentiation culture obtained by differentiating cells from hematopoietic stem cells.

In an aspect of the present invention, the amino acid contained in the cell culture medium of the present invention is one or more amino acid selected from the group consisting of essential amino acids, such as tryptophan, lysine, methionine, phenylalanine, threonine, leucine, isoleucine, and histidine, or all amino acids selected from the group consisting of the essential amino acids (provided that, the nutrients are free of valine or cysteine or both).

In an aspect of the present invention, the amino acids contained in the cell culture medium of the present invention are asparagine, aspartic acid, serine, threonine, glutamine, glutamic acid, proline, glycine, methionine, leucine, isoleucine, tyrosine, phenylalanine, histidine, alanine, lysine, tryptophan, and arginine.

In an aspect of the present invention, the amino acids contained in the cell culture medium of the present invention are asparagine, aspartic acid, serine, threonine, glutamine, glutamic acid, proline, glycine, methionine, leucine, isoleucine, tyrosine, phenylalanine, histidine, alanine, lysine, tryptophan, cysteine, and arginine.

In an aspect of the present invention, the amino acids contained in the cell culture medium of the present invention are asparagine, aspartic acid, serine, threonine, glutamine, glutamic acid, proline, glycine, methionine, leucine, isoleucine, tyrosine, phenylalanine, histidine, alanine, lysine, tryptophan, valine, and arginine.

In an aspect, the human cell culture medium of the present invention is free of one or more amino acids selected from the group consisting of alanine, cysteine, histidine, lysine, methionine, glutamine, and valine as amino acids, and preferably is free of cysteine or valine.

EXAMPLES

Example 1: Effect of Amino Acid Deletion in Cell Culture Medium

A cell culture medium comprising a deletion of 1 amino acid of the 20 amino acids was prepared to examine the effect of deletion of each amino acid on the growth of hematopoietic stem cells.

C57BL/6 (B6-Ly5.2) mice were purchased from Japan SLC Inc. and C57BL/6 (B6-Ly5.1) mice and NOD/scid (Ly5.2) mice were purchased from Sankyo Labs Service Corporation. Mice were housed according to the guidance of the University of Tokyo for animal and recombinant DNA experiments in the Animal Research Facility of the Institute of Medical Science, the University of Tokyo.

For the cell culture medium, amino acid-free RPMI1640 medium (product number: R8758) and DMEM/F12 medium (product number: D6421) were purchased from Sigma-Aldrich Corporation. These media were mixed in equal amounts. Amino acids were added to the medium as shown in FIG. 1. S-clone SF-O3 medium was purchased from Sanko Junyaku Co., Ltd.

The hematopoietic stem cells used were mouse CD34$^-$ KSL cells. The mouse CD34$^-$ KSL cells were collected from the bone marrow of 8- to 12-week-old C57BL/6 (B6-Ly5.1) mice. Specifically, bone marrow cells were stained with an allophycocyanin (APC)-conjugated anti-c-kit antibody (from eBioscience Co., Ltd.) and c-kit$^+$ cells were concentrated with anti-APC magnetic beads (from Miltenyi Biotech Co., Ltd.). The resultant cells were stained with a fluorescein isothiocyanate (FITC)-conjugated anti-CD34 antibody (from eBioscience Co., Ltd.) and a phycoerythrin (PE)-conjugated anti-Sca-1 antibody (from eBioscience Co., Ltd.), and further stained with an antibody cocktail of an anti-Gr-1 antibody, an anti-Mac-1 antibody, an anti-B220/CD45R antibody, an anti-CD4 antibody, an anti-CD8 antibody, an anti-CD127/IL7Rα antibody, and an anti-Ter-119 antibody (from eBioscience Co., Ltd.) as a lineage marker. Thereafter, the mouse CD34$^-$KSL cells were purified using a cell sorter from Becton, Dickinson and Company (BD).

The resultant hematopoietic stem cells were cultured at 40 cells/well in the 1-amino acid deletion cell culture medium (containing 1% bovine serum albumin, 50 ng/mL mouse SCF (from PeproTech Co., Ltd.), and 50 ng/mL mouse TPO) for 1 week, and the number of the cells after culture was counted. The experiment was independently repeated 3 times.

FIG. 2 shows photographs of the cells cultured in the amino acid deletion medium for 1 week. According to FIG. 2, no cell mass was observed in the cases of valine (−Val)

and cysteine (–Cys). The results of counting cells are as shown in FIG. 3. As shown in FIG. 3A, no cells increased in the cases of valine (–Val) and cysteine (–Cys).

This demonstrated that valine (–Val) or cysteine (–Cys) was necessary for the growth of hematopoietic stem cells.

Example 2: Transplantation of Hematopoietic Stem Cells Cultured in Amino Acid Deletion Medium Next, the hematopoietic stem cells cultured by the method of Example 1 were administered to irradiated mice, and the engraftment of the cells was identified.

The hematopoietic stem cells obtained by culture in Example 1 (referred to as donor hematopoietic stem cells) were used as the hematopoietic stem cells cultured in an amino acid deletion medium. The irradiated mice were obtained by irradiating C57BL/6 (B6-Ly5.2) mice with a dose of 9.5 Gy. To observe the growth of the cells under competitive conditions, $1 \times 10^6$ bone marrow cells (referred to as competitive cells) were obtained from Ly5.1 and Ly5.2 F1 mice.

The hematopoietic stem cells cultured in the amino acid deletion medium and the F1 mouse bone marrow cells were transplanted into the irradiated mice. To calculate the contribution rate (chimeric rate) of the donor hematopoietic stem cells, the peripheral blood (PB) was collected 12 weeks after transplantation, and the donor hematopoietic stem cells and the competitive cells were stained with a PE/Cy7-conjugated anti-Ly5.1 antibody (from Tonbo Co., Ltd.) and an FITC-conjugated anti-Ly5.2 antibody (from BioLegend Co., Ltd.), respectively. In addition, to calculate the proportions of B cells, T cells, bone marrow cells, and other cells, the peripheral blood was further stained with a PE-conjugated anti-Mac-1 antibody and an anti-Gr-1 antibody, an APC-conjugated anti-CD4 antibody and an anti-CD8 antibody, and an APC-eFluor 780-conjugated anti-B220/CD45R antibody.

The numbers of the donor hematopoietic stem cells and the competitive cells were counted using FACS Canto II (from Becton, Dickinson and Company) to determine the chimeric rate. The chimeric rate was determined by dividing the number of the donor hematopoietic stem cells by the sum of the numbers of the donor hematopoietic stem cells and the competitive cells.

The results are as shown in FIG. 3B. As shown in FIG. 3B, the chimeric rate was almost 0 in the cases of valine (–Val) and cysteine (–Cys).

Example 3: Analysis of Mouse Fed on Diet Free of Any of Amino Acids

In this Example, the presence or absence of abnormalities were analyzed in mice given diets free of valine or cysteine.

The diets had product numbers and compositions as described in FIG. 4 and were purchased from Research Diet Co., Ltd. First, the content of each amino acid was measured in the peripheral blood and bone marrow of mice fed on a conventional diet or a valine-free diet for 4 weeks.

A peripheral blood sample for the measurement of the amino acid content was obtained by centrifuging blood sampled from the eye socket to remove cell components and then removing protein components using Amicon Ultra-0.5 mL Centrifugal Filter (from Merck Millipore Co., Ltd.). A bone marrow sample for the measurement of the amino acid content was obtained by eluting the bone marrow with water and then removing protein using Amicon Ultra-0.5 mL Centrifugal Filter. The content of each amino acid in these samples was measured using Prominence Amino Acid Analysis System (from Shimadzu Corporation).

Figure 5:
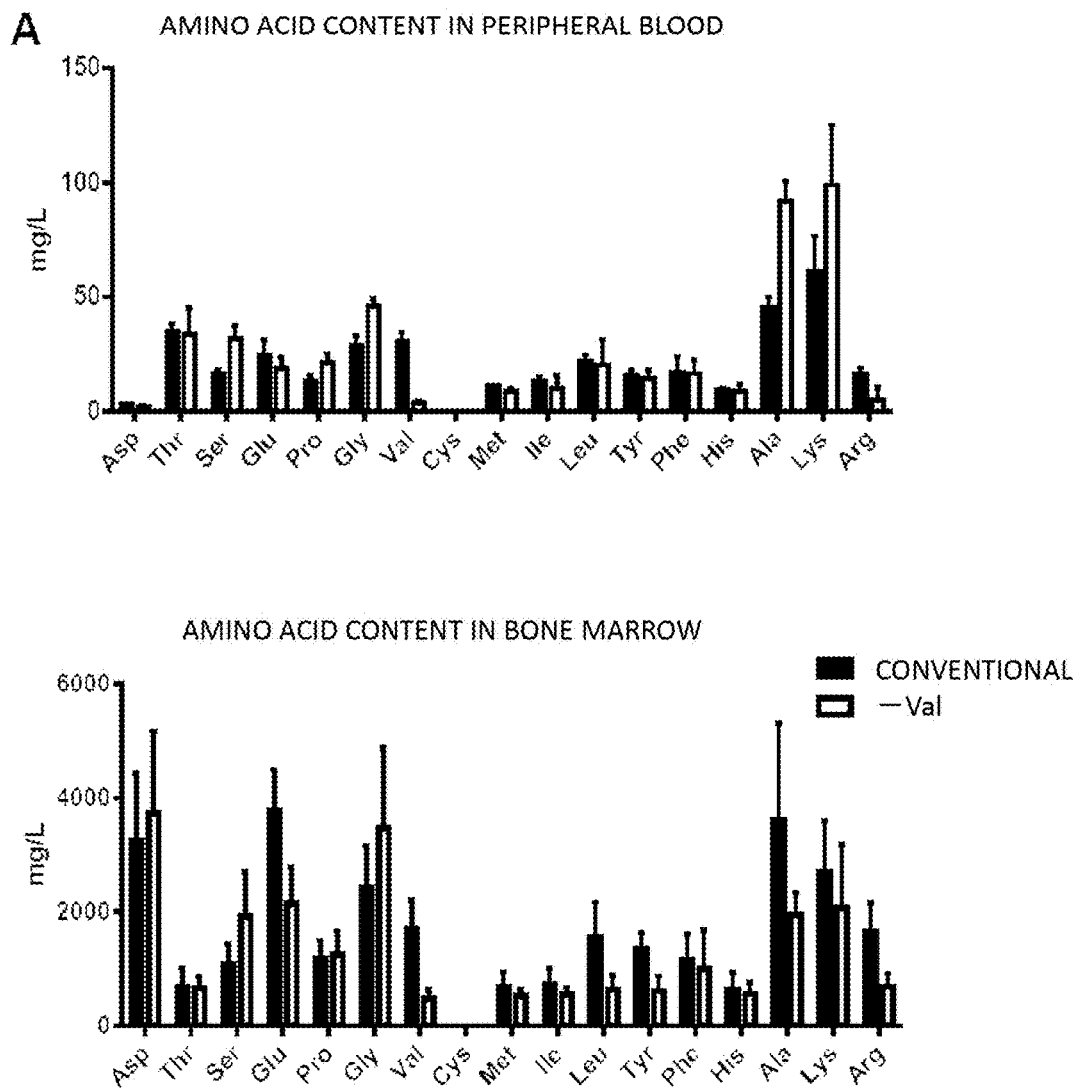
FIG. 5 shows the results of examining the content of amino acids in the peripheral blood and bone marrow of mice fed on a normal diet or a valine-free diet (−Val) for 4 weeks.

The results are as shown in FIG. 5. As shown in FIG. 5, the valine content decreased in the peripheral blood and in the bone marrow for mice given the valine-free diet for 4 weeks.

Figure 6:
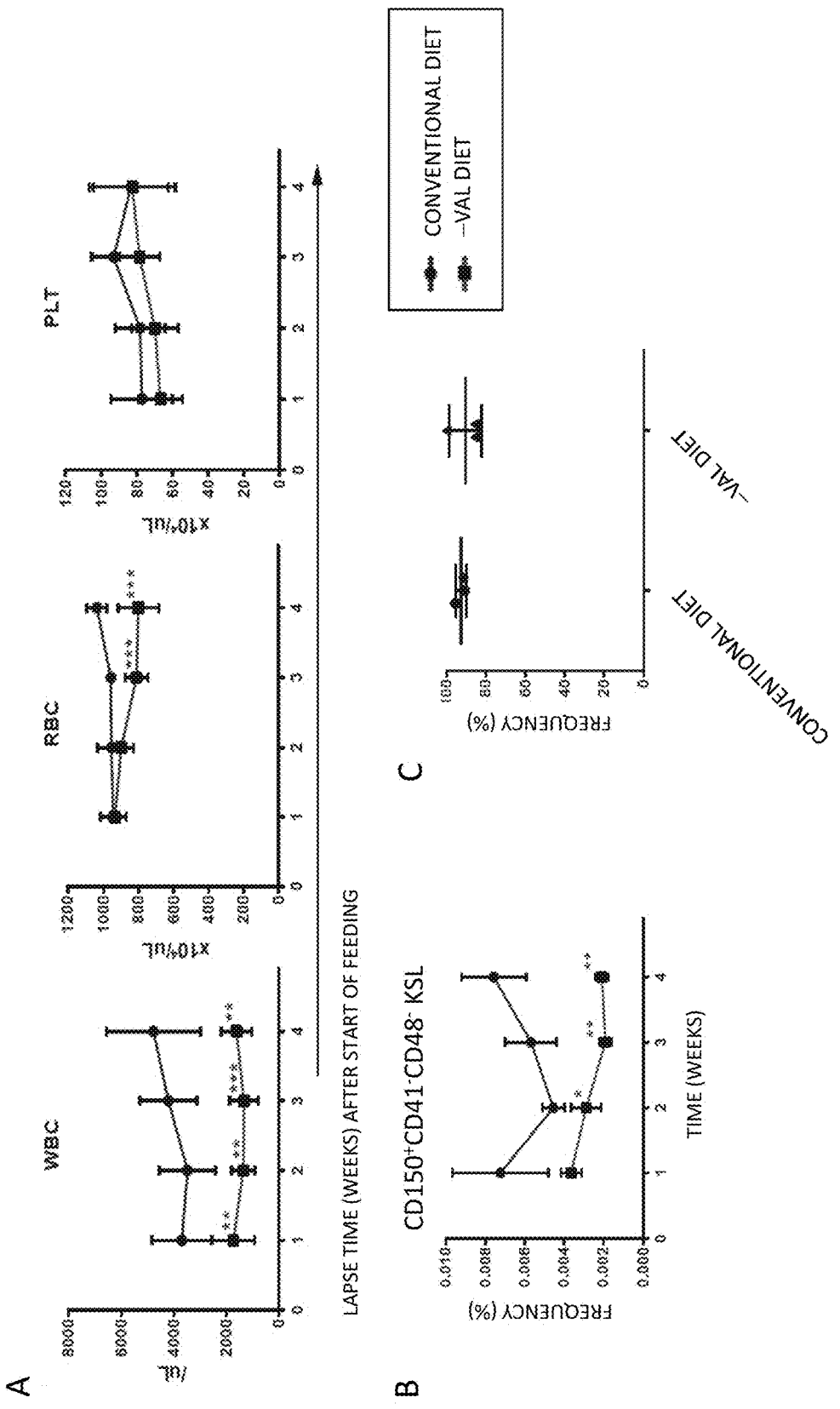
FIG. 6A shows the whole blood cell count (WBC), the red blood cell count (RBC) and the platelet count (PLT) in the peripheral blood sample obtained from mice given a normal diet or a valine-free diet for 4 weeks.
FIG. 6B shows the existence frequency of $CD150^+CD41^-CD48^-$ KSL cells in the bone marrow.
FIG. 6C shows the frequency of cells whose cell cycle is in the G0 stage.

Then, when the whole blood cell count (WBC), the red blood cell count (RBC), and the platelet count (PLT) in the peripheral blood sample obtained from the mice given a valine-free diet for 4 weeks were counted using an automated blood cell counter (MEK-6258) from Nihon Kohden Co., Ltd., a large decrease in the whole blood cell count was observed as shown in FIG. 6A. A significant difference was also observed in the red blood count.

In addition, the number of hematopoietic stem cells was examined in the mice given a valine-free diet for 4 weeks. As the hematopoietic stem cells, $CD150^-CD41^-CD48^-$ KSL cells were obtained by the following method. First, bone marrow cells were collected from B6 mice given a valine-free diet for 4 weeks. The cells were stained with the lineage marker cocktail, an APC-conjugated anti-c-kit antibody, a pacific blue-conjugated anti-Sca 1 antibody, an FITC-conjugated anti-CD41 antibody, an Alexa Fluor 488-conjugated anti-CD48 antibody, and PE-conjugated anti-CD150 antibody, and a streptavidin-APC-eFluor 780 antibody.

The number of the cells was counted using FACS Aria-2 (from BD Biosciences Co., Ltd.), and analysis was carried out using FlowJo Software (from Tree Star Inc.).

Figure 7:
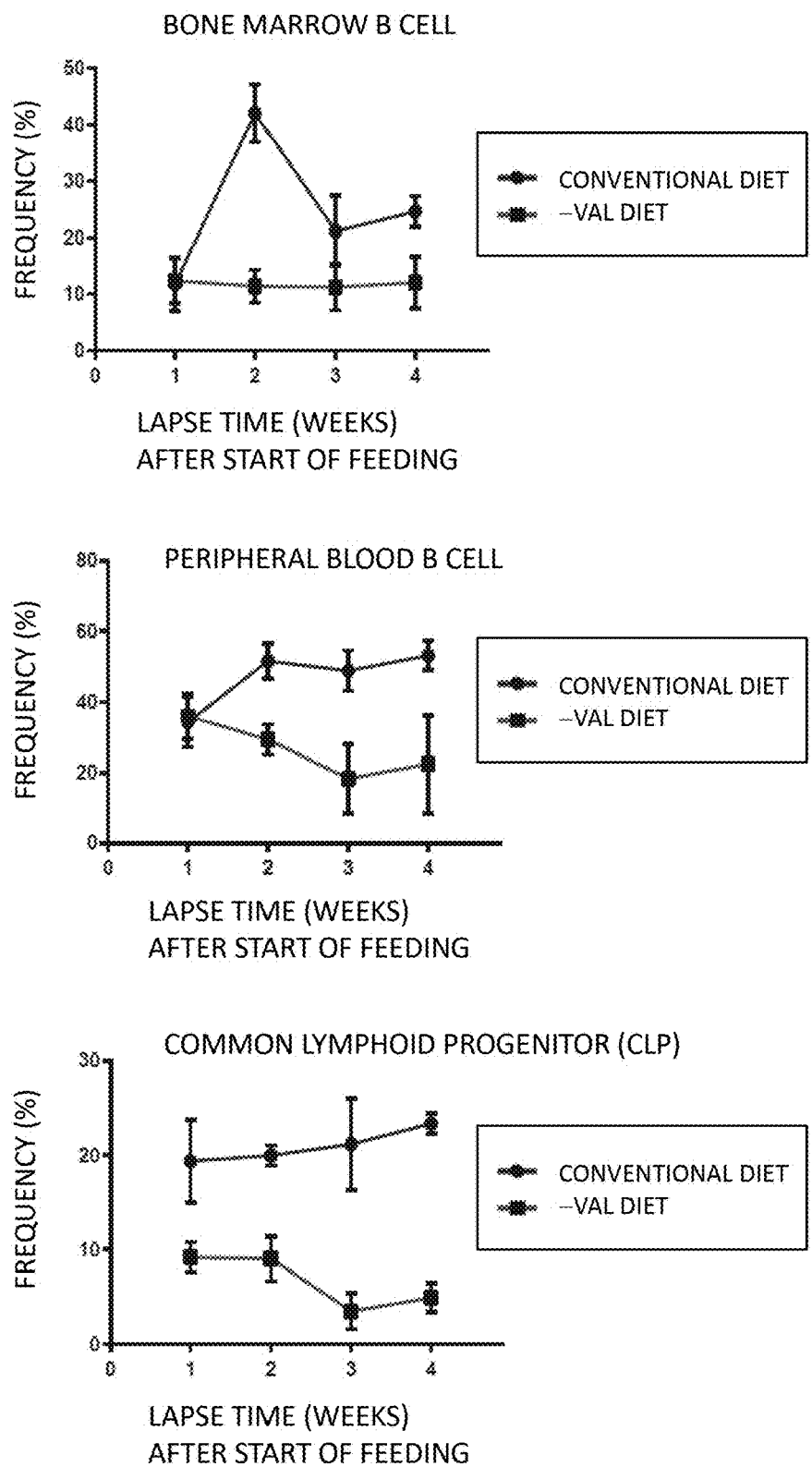
FIG. 7 shows the existence frequency of bone marrow B cells, peripheral blood B cells, and common lymphoid progenitors in mice given a normal diet or a valine-free diet.

As a result, as shown in FIG. 6B, the frequency of appearance of hematopoietic stem cells remarkably decreased in the mice given a valine-free diet. The examination of the expression of CD34 and the proportion of the cells in the G0 stage by pyronin Y staining resulted in that the proportion of the cells at the G0 stage was little changed between the mice given a valine-free diet and the mice given a conventional diet (FIG. 6C). A significant decrease in B cells was observed in each of the peripheral blood and bone marrow for the mice given a valine-free diet (FIG. 7). A significant decrease in the number of common lymphoid progenitors (CLP) was also observed for the mice given a valine-free diet (FIG. 7).

In addition, when the frequency of CD34 KSL hematopoietic stem cells was identified, the $CD34^-$ KSL hematopoietic stem cells significantly decreased in the mice given a valine-free diet for 4 weeks (FIG. 8).

Example 3: Effect of Diet Free of Any of Amino Acids on Mouse

In this Example, the survival rate of mice to which a diet free of any of the amino acids continued to be given was identified.

A diet free of any of shown amino acids continued to be given to C57BL/6 housed under fasting for 2 days to identify the survival rate.

Figure 9:
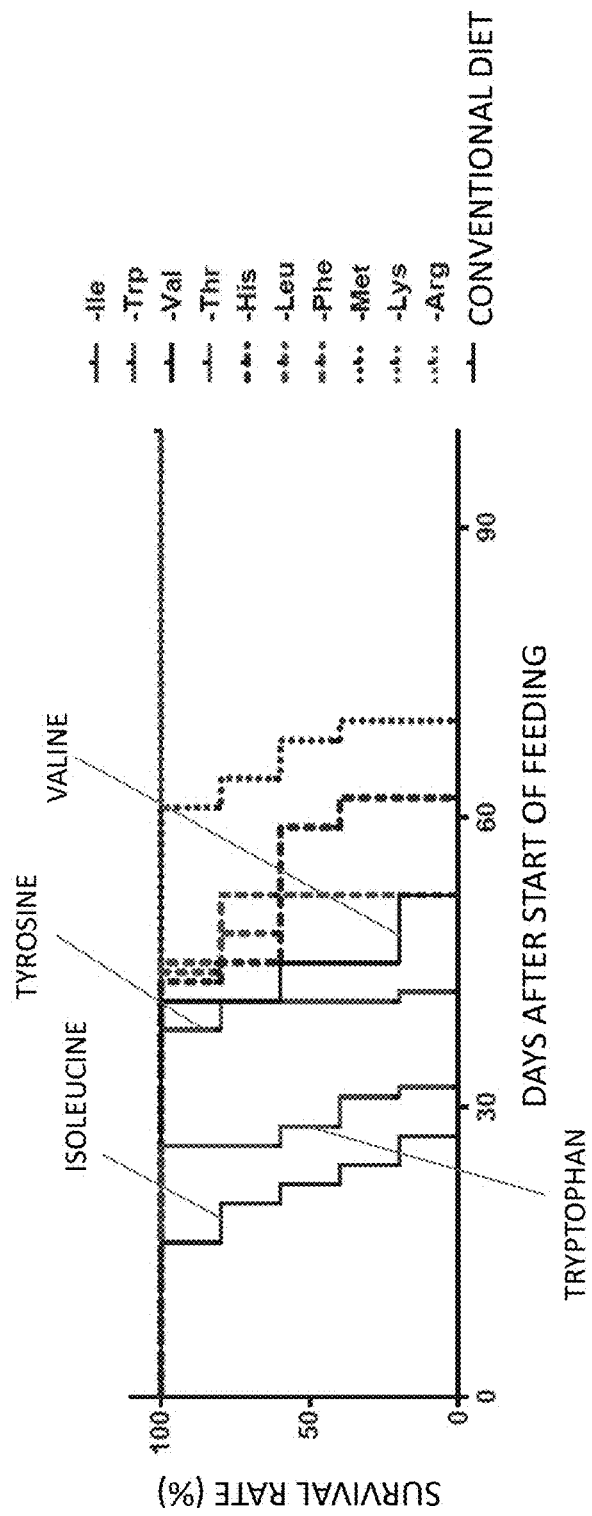
FIG. 9 shows the survival curve of mice fed on a diet free of any of the amino acids.

As a result, as shown in FIG. 9, all mice fed on an isoleucine-free diet or a tryptophan-free diet died in on the order of 1 month. The survival rate of mice was not affected for at least on the order of 40 days for mice fed on a diet free of valine.

Figure 10:
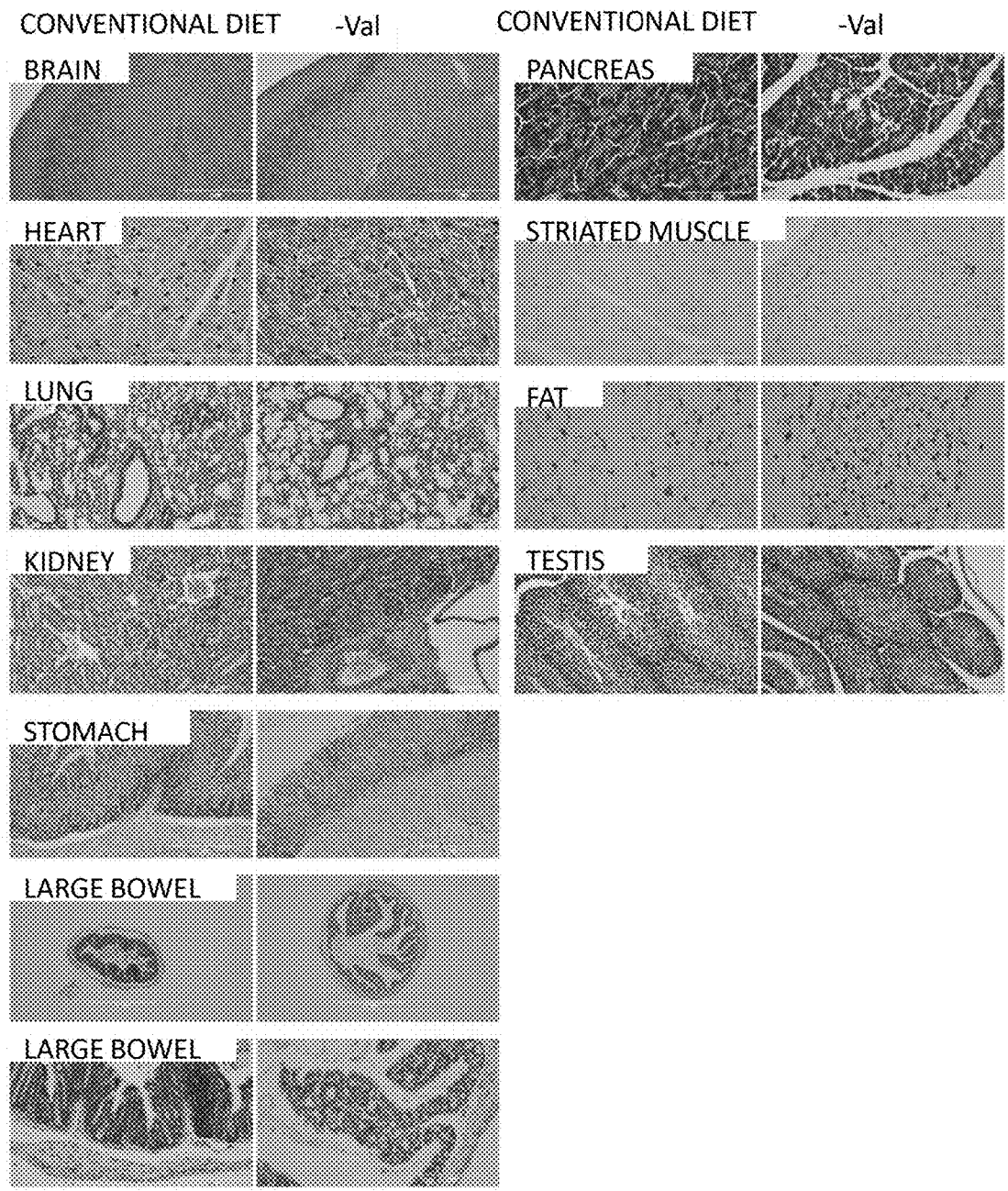
FIG. 10 illustrates photographs showing tissue section images in mice fed on a normal diet or a valine-free diet for 4 weeks.

In addition, sections of each tissue of mice fed on a valine-free diet for 4 weeks were examined. The sections were prepared by a conventional method, and ones subjected to hematoxylin-eosin staining were observed. As a result, as shown in FIG. 10, no difference could be observed in the brain, heart, lung, kidney, stomach, pancreas, and testis of the mice fed on a valine-free diet compared to in those of the mice fed on a conventional diet. On the other hand, the villi became longer in the large bowel and changes were observed in the striated muscle and brown fat cells (FIG. 10).

Next, the mice were fed on a valine-free diet for 1, 2, 3, or 4 weeks and then returned to a conventional diet for feeding to identify the transition of a change in the body weight of mice and the size of the spleen and the thymus. As a result, as shown in FIG. 11A, the mice fed on a valine-free diet did not have an increase in body weight but showed a rapid recovery in the body weight when returned to a conventional diet for feeding.

As shown in FIGS. 11B and 11C, feeding on a valine-free diet for 4 weeks reduced the spleen and the thymus in size; however, returning to a conventional diet for feeding for 4 weeks causes the size of the spleen and the thymus to recover to the same as that of mice persistently fed on a conventional diet.

This suggests that even when hematopoietic stem cells in the body of a patient are eliminated with a valine-free meal while maintaining the life of the patient, subsequently giving a conventional meal containing valine enables recovery from the effect of the valine deletion.

Example 4: Effect of Valine-Free Diet on Long-Term Hematopoiesis

In this Example, the engraftment rate of the total bone marrow of mice fed on a valine-free diet was examined under competitive conditions of transplanting the total bone marrow of the mice fed on a valine-free diet and the total bone marrow of the mice fed on a conventional diet in equal amounts into the body of irradiated mice.

The irradiated mice were obtained by exposing C57BL/6 (Ly5.2) mice to a lethal dose of radiation. C57BL/6 (Ly5.1) mice were fed on a valine-free diet for 4 weeks, followed by obtaining the total bone marrow. B6 (Lv5.1/Ly5.2) mice were also fed on a conventional diet for 4 weeks, followed by obtaining the total bone marrow.

Equal amounts of the total bone marrows were transplanted into the irradiated mice under competitive conditions, and hematopoiesis from each of the total bone marrows was identified by the chimeric rate of blood cells.

Figure 12:
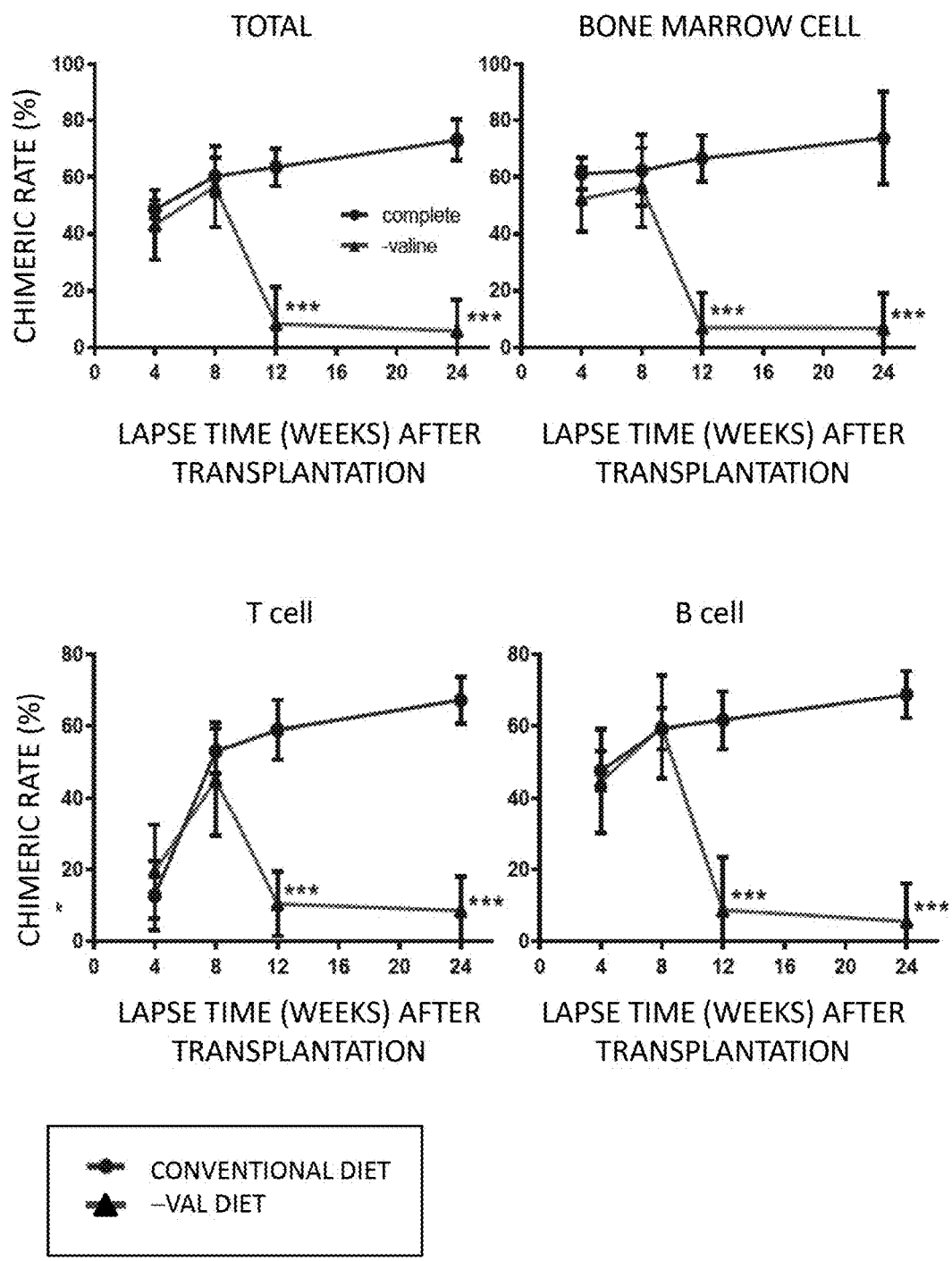
FIG. 12 shows the transition of the chimeric rate by transplanting the total bone marrow obtained from mice fed on a normal diet or a valine-free diet into irradiated mice under competitive conditions.

As a result, as shown in FIG. 12, a significant decrease was not observed at about 8 weeks after transplantation in each of the whole blood cells, bone marrow cells, T cells, and B cells, but cells derived from the total bone marrow of the mice fed on a valine-free diet were little observed at about 12 weeks after transplantation.

This suggests that the blood cell system, particularly hematopoietic stem cells, was affected by the valine-free diet.

Example 5: Effect of Valine-Free Diet on Division of Hematopoietic Stem Cell

In this Example, the effect of valine depletion on the division of hematopoietic stem cells was examined.

Figure 13:
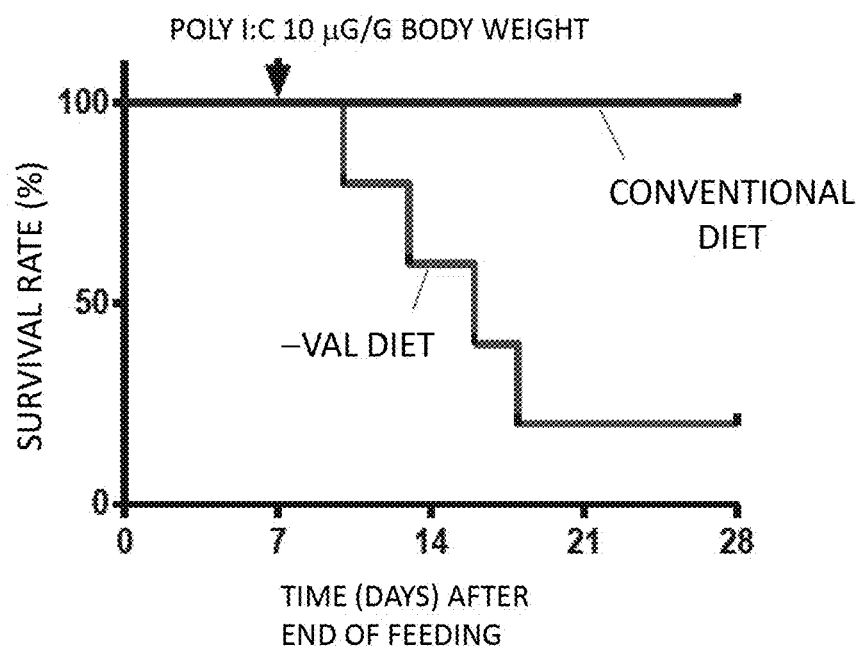
FIG. 13 shows the survival rate after administering poly I:C to mice fed on a normal diet or a valine-free diet (−Val) for 2 weeks.

C57BL/6 mice was fed on a valine-free diet for 2 weeks, and after further 7 days, poly I:C was intraperitoneally administered. As a result, as shown in FIG. 13, the mice fed on the valine-free diet died from 3 days after administration. Poly I:C is known to forcibly divide cells by inducing interferon-1. Thus, this result suggests that valine is necessary for the division of cells.

Example 6: Hematopoietic Stem Cell Transplantation Experiment

Donor-derived hematopoietic stem cells are typically transplanted into a recipient of the hematopoietic stem cell transplantation after eliminating hematopoietic stem cells by irradiation. In this Example, hematopoietic stem cells in the body of a recipient were decreased by giving a valine-free diet; donor-derived hematopoietic stem cells were then transplanted; and the engraftment of the donor-derived hematopoietic stem cells was identified.

Specifically, as shown in FIG. 14A, NOD/SCID mice (Ly5.1) as a recipient were fasted for 2 days and then fed on a conventional diet or a valine-free diet for 2 weeks, and $5 \times 10^3$ KSL cells derived from B6 mice (Ly5.2) as a donor were transplanted into the recipient, followed by feeding on the conventional diet and monitoring the chimeric rate of hematopoietic stem cells for 3 months.

As a result, as shown in FIG. 14B, no engraftment of donor cells was observed in the mice fed on the conventional diet for 2 weeks, whereas the engraftment of donor cells was observed in the mice fed on the valine-free diet for 2 weeks.

As shown in FIG. 14C, the engraftment of donor cells was identified in all except 4 dead mice of the 10 mice fed on the valine-free diet for 2 weeks. T cells, B cells, and bone marrow cells were identified in the recipient mice at 1 month after transplantation (FIG. 14C).

This showed that although donor-derived hematopoietic stem cells were transplanted after eliminating recipient-derived hematopoietic stem cells by irradiation in a conventional method for hematopoietic stem cell transplantation, feeding alone on a valine-free diet in place of irradiation enabled the engraftment of donor-derived transplanted hematopoietic stem cells.

Example 7: Effect of Valine Depletion on Human Hematopoietic Stem Cell $CD34^+CD38^-Lin^-$ hematopoietic stem cells were obtained from the umbilical cord blood by a conventional method. The resultant human hematopoietic stem cells were cultured in a medium free of any of the amino acids (containing SCF, TPO, Flt3L, IL-3, and IL-6) for 10 days, and assayed for colonies using a methylcellulose medium by a conventional method.

Figure 15:
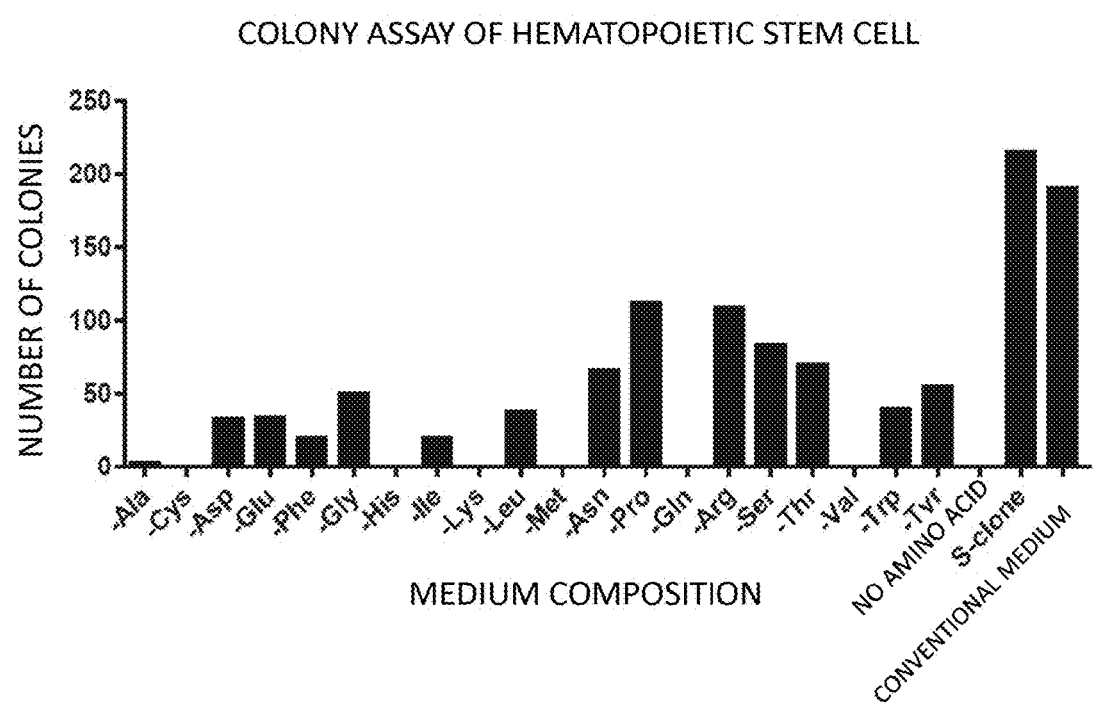
FIG. 15 shows the effect of an amino acid deletion medium on human hematopoietic stem cells.

The results are as shown in FIG. 15. The human hematopoietic stem cells could not form colonies when cultured in the valine-free medium. The human hematopoietic stem cells could not also form colonies when cultured in a medium free of cysteine, histidine, lysine, methionine, or glutamine.

The invention claimed is:

1. A method, comprising:
   administering a nutrition formula sufficient to a subject for a period of time to decrease hematopoietic stem cells in the subject, and
   detecting a decrease in the number of hematopoietic stem cells in the subject,
   wherein the nutrition formula is a complete nutrition formulation except for being substantially free of valine and
   a subject's diet is restricted to the nutrition formula only during the administrating period.
2. The method of claim 1, further comprising:
   transplanting hematopoietic stem cells to the subject, wherein the detecting comprises confirming the decrease in the number of hematopoietic stein cells in the subject.

3. The method of claim 2, further comprising:
administering a conventional nutrition formula to the subject after the administering the nutrition formula wherein the nutrition formula is a complete nutrition formulation except for being substantially free of valine.

4. The method of claim 1, wherein the detecting comprises:
(a) counting the number of hematopoietic stem cells in a bone marrow fluid or peripheral blood sample obtained from the subject before the administering;
(b) counting the number of hematopoietic stem cells in a bone marrow fluid or peripheral blood sample obtained from the subject during the administering or after the administering; and
(c) comparing the number of the cells determined in (a) and the number of the cells obtained in (b).

5. The method of claim 1, wherein the nutrition formula comprises:
a sugar,
an electrolyte and
amino acids except for valine;
optionally a vitamin.

6. The method of claim 1, wherein the subject is a human.

7. The method of claim 1, wherein the detecting comprising detecting a decrease in hematopoietic stem cells in a bone marrow fluid obtained from the subject.

8. The method of claim 1, wherein the detecting comprising detecting a decrease in hematopoietic stem cells in a peripheral blood sample obtained from the subject.

9. The method of claim 1, wherein the nutrition formula is a complete parenteral nutrition formulation except for being substantially free of valine.

10. The method of claim 1, wherein the nutrition formula is a complete enteral nutrition formulation except for being substantially free of valine.

11. The method of claim 1, wherein the nutrition formula is a complete nutrition formulation except for being substantially free of valine and cysteine.

12. The method of claim 1, wherein the decrease in the detecting is a decrease of the hematopoietic stem cells by 90%.

* * * * *